US012690862B2

(12) United States Patent
Tsui et al.

(10) Patent No.:  US 12,690,862 B2
(45) Date of Patent:      Jul. 28, 2026

(54) SURGICAL SUTURE HOLDER

(71) Applicant: 3R LIFE SCIENCES CORPORATION, Campbell, CA (US)

(72) Inventors: Steven Shi Lap Tsui, Campbell, CA (US); Pong-Jeu Lu, Campbell, CA (US)

(73) Assignee: 3R LIFE SCIENCES CORPORATION, Campbell, CA (US)

( * ) Notice: Subject to any disclaimer, the term of this patent is extended or adjusted under 35 U.S.C. 154(b) by 309 days.

(21) Appl. No.: 18/446,324

(22) Filed: Aug. 8, 2023

(65) Prior Publication Data

US 2025/0049435 A1      Feb. 13, 2025

(51) Int. Cl.
*A61B 17/06*          (2006.01)

(52) U.S. Cl.
CPC .............................. *A61B 17/06061* (2013.01)

(58) Field of Classification Search
CPC .......................... A61B 17/06114–06138; A61B 2017/06142–06157; A61B 17/06; A61B 17/06061; A61B 17/0483
USPC ........................................................ 606/148
See application file for complete search history.

(56) References Cited

U.S. PATENT DOCUMENTS

| | | | | |
|---|---|---|---|---|
| 4,185,636 | A * | 1/1980 | Gabbay ................. | A61F 2/2427 24/339 |
| 4,823,794 | A * | 4/1989 | Pierce ................ | A61B 17/0401 606/232 |
| 2003/0204195 | A1* | 10/2003 | Keane ................ | A61B 17/0401 606/146 |
| 2009/0192468 | A1* | 7/2009 | Stone .................... | A61F 2/0805 606/151 |
| 2010/0016890 | A1* | 1/2010 | Tsai ..................... | D06B 23/042 606/228 |
| 2010/0292732 | A1* | 11/2010 | Hirotsuka ............... | B29C 45/00 606/232 |
| 2017/0135691 | A1* | 5/2017 | Branthover ........ | A61B 17/0401 |
| 2017/0172570 | A1* | 6/2017 | Wentling ............. | B65D 5/4266 |
| 2017/0319202 | A1* | 11/2017 | Marczyk .......... | A61B 17/06061 |
| 2020/0268382 | A1* | 8/2020 | Vailhe .............. | A61B 17/06114 |

* cited by examiner

*Primary Examiner* — Elizabeth Houston
*Assistant Examiner* — Serenity A Miller
(74) *Attorney, Agent, or Firm* — HSML P.C.

(57)          ABSTRACT

A surgical suture holder is adapted to be disposed on an opening of a tubular snaring object, is adapted for holding at least one surgical suture, extends along a holder axis, and includes an insertion section and a holding section. The insertion section is adapted to be inserted into the opening of the tubular snaring object and being tapered toward the tubular snaring object. The holding section has a holding board that has a periphery surrounding the holder axis, and at least one holding slot that is recessed from the periphery of the holding board, that extends through the holding board in an extending direction of the holder axis, and that is adapted for the at least one surgical suture to fit thereinto so that the holding slot holds the at least one surgical suture.

7 Claims, 6 Drawing Sheets

SURGICAL SUTURE HOLDER

FIELD

The disclosure relates to a surgical suture holder, and more particularly to a cardiovascular surgical suture holder for a tubular snaring object.

BACKGROUND

During surgery (e.g., cardiovascular surgery, or cardiac surgery involving cardiac cannula fixation), a conventional hemostatic clamp is commonly used to hold a surgical suture by clamping a rubber hose (snaring tube) through which the surgical suture extends. However, the conventional hemostatic clamp takes up much space in areas near an incisive opening or a thoracic surgical field. If the incisive opening is relatively small or the thoracic surgical field needs to be temporarily closed, a surgeon may have difficulty in using the conventional hemostatic clamp, especially when the surgery involves a plurality of conventional hemostatic clamps. To carry out the surgery using the conventional hemostatic clamps, the surgeon may have to make the incisive opening bigger than necessary or leave the thoracic surgical field partially closed, which may result in higher risk of infection or longer recovery time for a patient.

SUMMARY

An object of the disclosure is to provide a surgical suture holder that can alleviate at least one of the drawbacks of the prior art in the category of cardiac or cardiovascular surgery.

According to the disclosure, the surgical suture holder is adapted to be disposed on an opening of a tubular snaring object, is adapted for holding at least one surgical suture, and extends along a holder axis. The surgical suture holder includes an insertion section and a holding section. The insertion section is adapted to be inserted into the opening of the tubular snaring object and is tapered toward the tubular snaring object. The holding section has a holding board that has a periphery surrounding the holder axis, and at least one holding slot that is recessed from the periphery of the holding board, that extends through the holding board in an extending direction of the holder axis, and that is adapted for the at least one surgical suture to fit thereinto so that the holding slot holds the at least one surgical suture.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
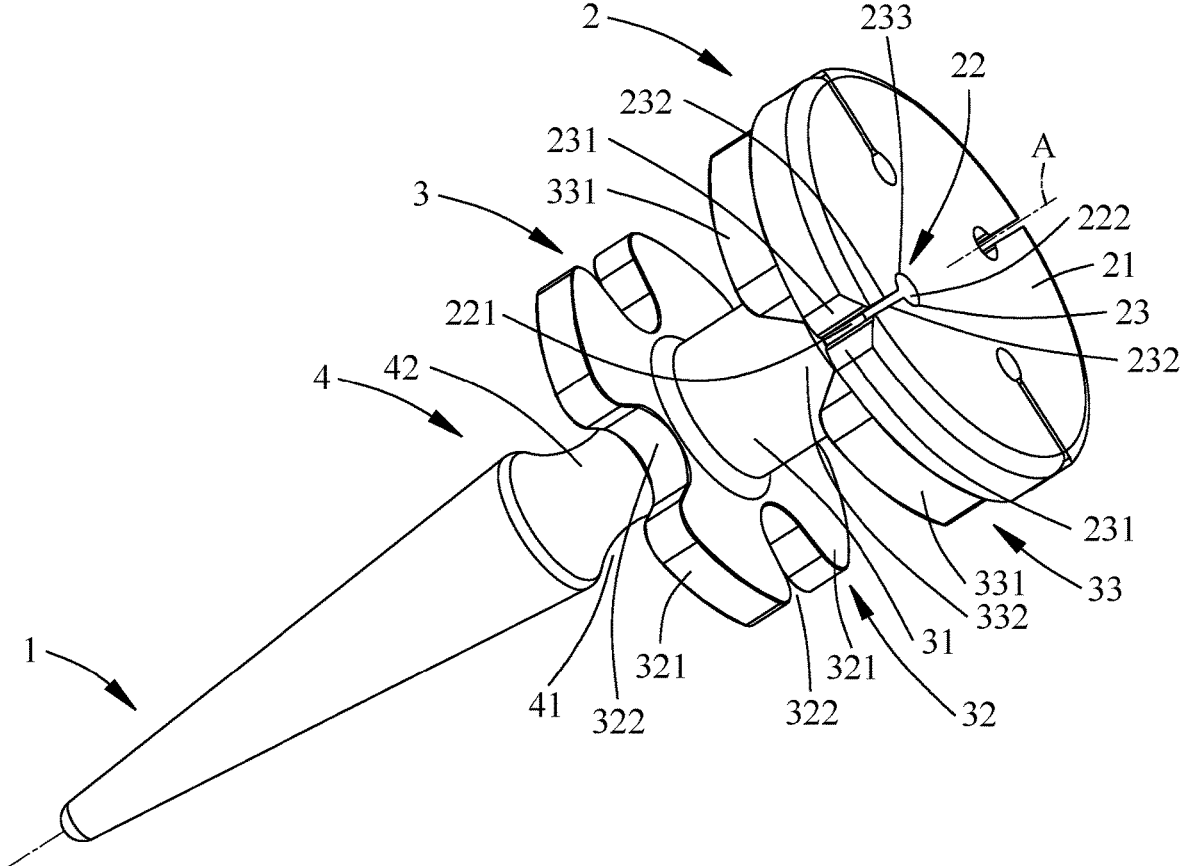
FIG. 1 is a perspective view of an embodiment of a surgical suture holder according to the disclosure.
Figure 2:
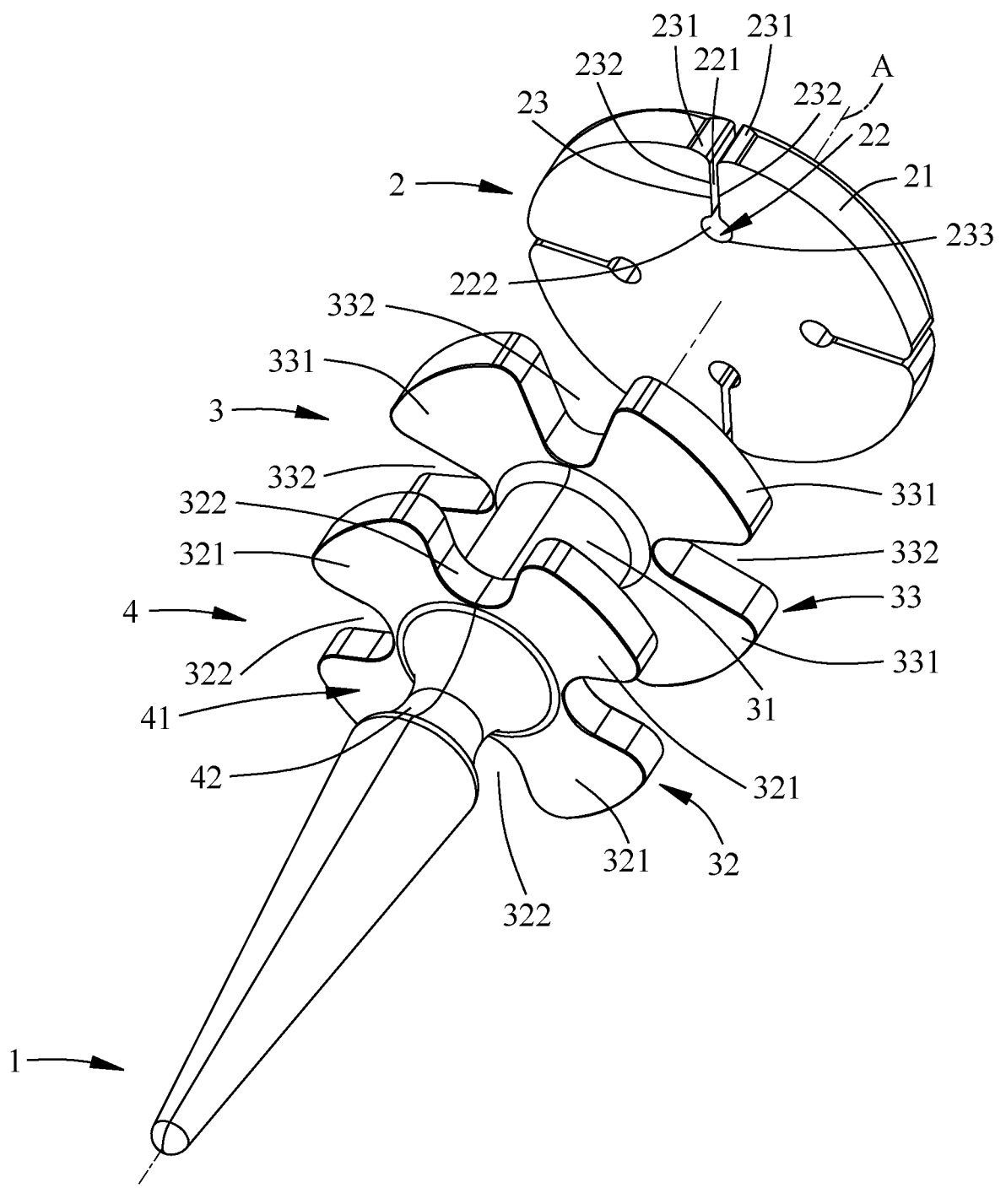
FIG. 2 is an exploded perspective view of the embodiment.
Figure 3:
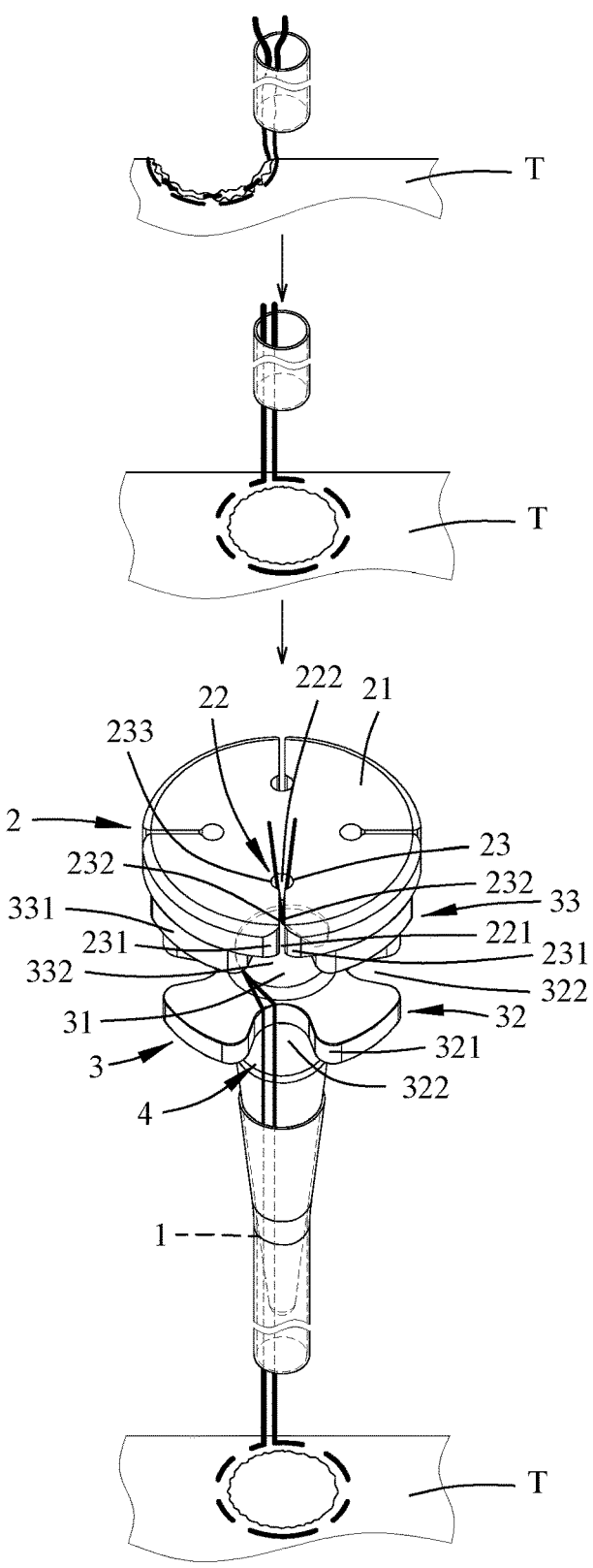
FIG. 3 is a schematic view illustrating the embodiment holding a surgical suture.

Referring to FIGS. 1 to 3, an embodiment of a surgical suture holder according to the disclosure is adapted to be disposed on an opening of a tubular snaring object, is adapted for holding a surgical suture, and extends along a holder axis (A). The surgical suture holder includes an insertion section 1, a holding section 2, a winding section 3, and a cutting section 4. The tubular snaring object may be a rubber hose that is used in surgery (e.g., cardiovascular surgery, or cardiac surgery involving cardiac bypass cannulae). The surgical suture has two end sections, and an interconnecting section that interconnects the end sections. This interconnecting section of the surgical suture may extend through a patient's body tissue (T), i.e., the patient's body tissue (T) is sewn up by the interconnecting section of the surgical suture. The end sections of the surgical suture may extend through the tubular snaring object such that two ends of the surgical suture are located at one side of the tubular snaring object opposite to the interconnecting section.

FIG. 3 illustrates a purse-string suture technique. First, the interconnecting section of the surgical suture extends in and out the patient's body tissue (T) along an edge of an opening of the patient's body tissue (T) such that the opening of the patient's body tissue (T) is surrounded by the interconnecting section of the surgical suture. The end sections of the surgical suture extend through the tubular object. Then, the end sections of the surgical suture is pulled away from the body tissue (T) so as to narrow/close the opening of the patient's body tissue (T). Afterwards, when the surgical suture is tightened, the surgical suture holder is disposed on the opening of the tubular object to hold the surgical suture.

The insertion section 1 is adapted to be inserted into the opening of the tubular snaring object, and is tapered toward the tubular snaring object to ease the insertion into the tubular snaring object. In this embodiment, the insertion section 1 is configured to be cone-shaped. In one embodiment, the insertion section 1 may have a different shape as long as the insertion section 1 is tapered toward the tubular snaring object.

The holding section 2 has a holding board 21, on which at least one holding slot 22, and at least one slot-defining surface 23 are made. In the present embodiment, the holding section 2 has four holding slots 22 and four slot-defining surfaces 23. The holding board 21 is configured to be disc-shaped, has a periphery that surrounds the holder axis (A), and is made of a resilient material so that the holding board 21 is deformable. Each of the slot-defining surfaces 23 defines a respective one of the holding slots 22. Each of the holding slots 22 is recessed from the periphery of the holding board 21, extends through the holding board 21 in an extending direction of the holder axis (A), and is adapted for the surgical suture to fit thereinto so that the surgical suture may be held by any one of the holding slots 22. Each of the holding slots 22 has a slot neck part 221 and a slot head part 222. The slot neck part 221 of each of the holding slots 22 is connected to the periphery of the holding board 21, and has a width adapted to be smaller than a diameter of the surgical suture before the holding board 21 is deformed. The slot head part 222 of each of the holding slots 22 is in spatial communication with the slot neck part 221 of the holding slot 22, and is adapted for accommodating the surgical suture.

Each of the slot-defining surfaces 23 has two guiding parts 231, two neck-defining parts 232, and a head-defining part 233. The guiding parts 231 are located at the periphery of the holding board 21, and are spaced apart from each other. The neck-defining parts 232 of each of the slot-defining surfaces 23 are respectively connected to the guiding parts 231 of the slot-defining surface 23, and are spaced apart from each other to cooperatively define the slot neck part 221 of the respective one of the holding slots 22. The head-defining part 233 of each of the slot-defining surfaces 23 interconnects the neck-defining parts 232 of the slot-defining surface 23, and defines the slot head part 222 of the respective one of the holding slots 22. The guiding parts 231 of each of the slot-defining surfaces 23 are adapted for guiding the surgical suture such that the surgical suture may easily be moved into the slot neck part 221 of the respective one of the holding slots 22. That is to say, the surgical suture may be guided into the slot head part 222 of one of the holding slots 22 by the guiding parts 231 of the respective one of the slot-defining surfaces 23 that defines the one of the holding slots 22.

The winding section 3 is located between the insertion section 1 and the holding section 2, and includes a winding portion 31, a first blocking board 32, and a second blocking board 33. The winding portion 31 is adapted to be wound around by the surgical suture, and interconnects the first blocking board 31 and the second blocking board 33. The first blocking board 32 is located between the winding portion 31 and the insertion section 1, and the second blocking board 33 is located between the winding portion 31 and the holding section 2. The first blocking board 32 has a board body 321 and at least one groove 322. In this embodiment, the first blocking board 32 has four grooves 322. In this embodiment, the holding board 21 and the second blocking board 33 are made of different materials to increase friction between the holding board 21 and the second blocking board 33. In one embodiment, the holding board 21 and the second blocking board 33 may be integrally formed. The board body 321 has a periphery that surrounds the holder axis (A). Each of the grooves 322 is recessed from the periphery of the board body 321, and extends through the board body 321 in the extending direction of the holder axis (A). The second blocking board 33 has a board body 331 and at least one groove 332. The holding board 21 is disposed on one side of the board body 331 of the second blocking board 33 opposite to the winding portion 31. In this embodiment, the second blocking board 33 has four grooves 332. The board body 331 has a periphery that surrounds the holder axis (A). Each of the grooves 332 is recessed from the periphery of the board body 331, extends through the board body 331 in the extending direction of the holder axis (A), and is in spatial communication with a respective one of the holding slots 22 of the holding section 2. The grooves 332 of the second blocking board 33 respectively correspond in position to the holding slots 22 in the extending direction of the holder axis (A). The grooves 322 of the first blocking board 32 respectively correspond in position to the holding slots 22 in the extending direction of the holder axis (A) such that the grooves 322 respectively correspond in position to the grooves 332 in the extending direction of the holder axis (A). Consequently, when the surgical suture is held by one of the holding slots 22, the surgical suture extends through the respective one of grooves 332 and the respective one of the grooves 322.

The cutting section 4 is located between the insertion section 1 and the winding section 3, and has a concave surface 42 that defines a cutting recess 41. The concave surface 42 surrounds the holder axis (A) such that an area of a cross section of the cutting section 4 decreases and then increases as the cutting section 4 extends from the insertion section 1 to the winding section 3. When the surgical suture is held by one of the holding slots 22 and extends through the respective one of grooves 332 and the respective one of the grooves 322, the surgical suture extends across the cutting recess 41. By virtue of the area of the cross section of the cutting section 4 decreasing and then increasing as the cutting section 4 extends from the insertion section 1 to the winding section 3, the surgical suture hangs over the concave surface 42 when the surgical suture extends across the cutting recess 41.

It is noted that, in this embodiment, the surgical suture holder has four holding slots 22, four grooves 322, and four grooves 332. The interconnecting section of each of the surgical sutures extends through the patient's body tissue (T), and the end sections of each of the surgical sutures extend through the tubular snaring object. The winding portion 31 may be wound around by the surgical sutures. When there are four surgical sutures, each of the surgical sutures is held by a respective one of the holding slots 22, extends through a respective one of the grooves 322 and a respective one of the grooves 332, and extends across the cutting recess 41. However, in one embodiment, the surgical suture holder may only have one holding slot 22, one groove 322, and one groove 332 such that one surgical suture is held by the holding slot 22, extends through the groove 322 and the groove 332, and extends across the cutting recess 41. In another embodiment of the surgical suture holder, the holding slots 22, the grooves 322, and the grooves 332 come in the same quantity, which may be any number other than those mentioned (i.e., four or one) in the above examples. Furthermore, each of the holding slots 22 may hold more than one surgical suture (i.e., in this embodiment, the surgical suture holder may hold more than four surgical sutures at a time).

It is noted that, in one embodiment, the surgical suture holder may be adapted for holding at least one surgical tape. When the surgical suture holder is used for holding a surgical tape, the slot neck part 221 of one of the holding slots 22 that holds the surgical tape has a width adapted to be smaller than a width of the surgical tape before the holding board 21 is deformed, and the slot head part 222 of the one of the holding slots 22 is adapted for accommodating the surgical tape. In another embodiment, the surgical suture holder may be adapted for holding at least one surgical tape and at least one surgical suture at a time.

Figure 4:
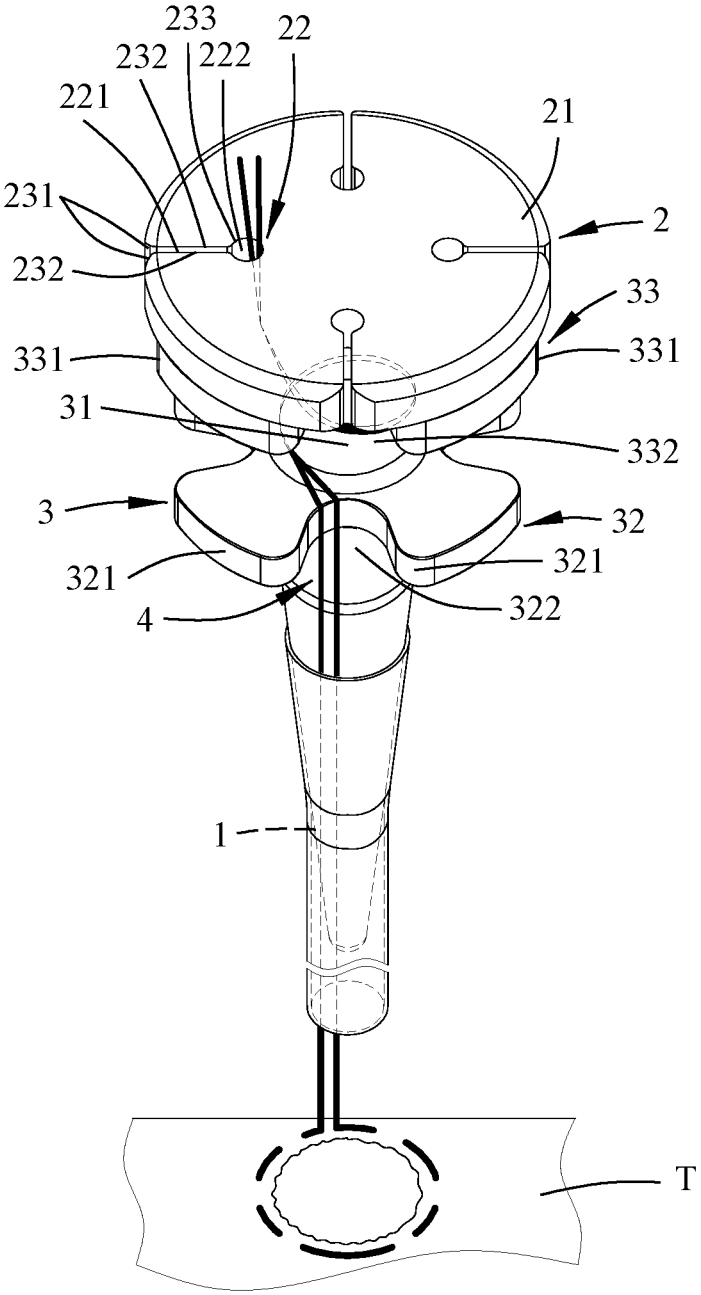
FIG. 4 is a schematic view illustrating the embodiment holding the surgical suture in a different manner.

Generally, the surgical suture holder is used for holding one surgical suture at a time. When using the surgical suture holder after the patient's body issue (T) is sewn up by the interconnecting section of the surgical suture, a user pulls the end sections of the surgical suture that extend through the tubular snaring object to increase tension in the surgical suture. At this time, a needle holder or a clamp is used to clamp the tubular snaring object and the end sections of the surgical suture that pass through the tubular snaring object. Then, the user plugs the opening of the tubular snaring object with the insertion section 1 of the surgical suture holder while pulling the end sections of the surgical suture to maintain the tension of the surgical suture stored between the opening of the tubular snaring object and the patient's body issue (T). The needle holder or the clamp is removed after the insertion section 1 of the surgical suture holder is securely inserted into the opening of the tubular snaring object. Afterwards, the user may further pull tight the end sections of the surgical suture and wind the end sections of the surgical suture around the winding portion 31 of the winding section 3 such that the end sections of the surgical suture extend across the cutting recess 41, hang over the concave surface 42, and extend through one of the grooves 322 of the winding section 3. Then, the user engages the end sections of the surgical suture into the respective one of the holding slots 22. The guiding parts 231 of the respective one of the slot-defining surfaces 23 that defines the respective one of the holding slots 22 guide the end sections of the surgical suture into the slot neck part 221 of the respective one of the holding slots 22. At this time, because the holding board 21 is made of the resilient material, the holding board 21 is resiliently deformed so that the end sections of the surgical suture may be moved through the slot neck part 221 of the respective one of the holding slots 22 in a radial direction of the holding board 21 toward the slot head part 222 of the holding slot 22 and then be accommodated in the slot head part 222 of the holding slot 22. When the end sections of the surgical suture are accommodated in the slot head part 222 of the respective one of the holding slots 22, the holding board 21 returns to its initial state (i.e., the holding board 21 is not deformed). By virtue of the width of the slot neck part 221 of the respective one of the holding slots 22 being smaller than the diameter of the surgical suture, the end sections of the surgical suture are prevented from moving radially outwardly from the holding board 21. The end sections of the surgical suture are thus held by the respective one of the holding slots 22. At this time, the end sections of the surgical suture extend through the respective one of the grooves 332 of the second blocking board 33. Referring further to FIG. 4, it is noted that, to further assure holding effectiveness, after the user winds the end sections of the surgical suture around the winding portion 31 of the winding section 3, the user may engage the end sections of the surgical suture into another one of the holding slots 22 such that the another one of the holding slots 22 holds the surgical suture and that the surgical suture extends through another groove 332 which corresponds in position to the another one of the holding slots 22 in the extending direction of the holder axis (A).

Figure 5:
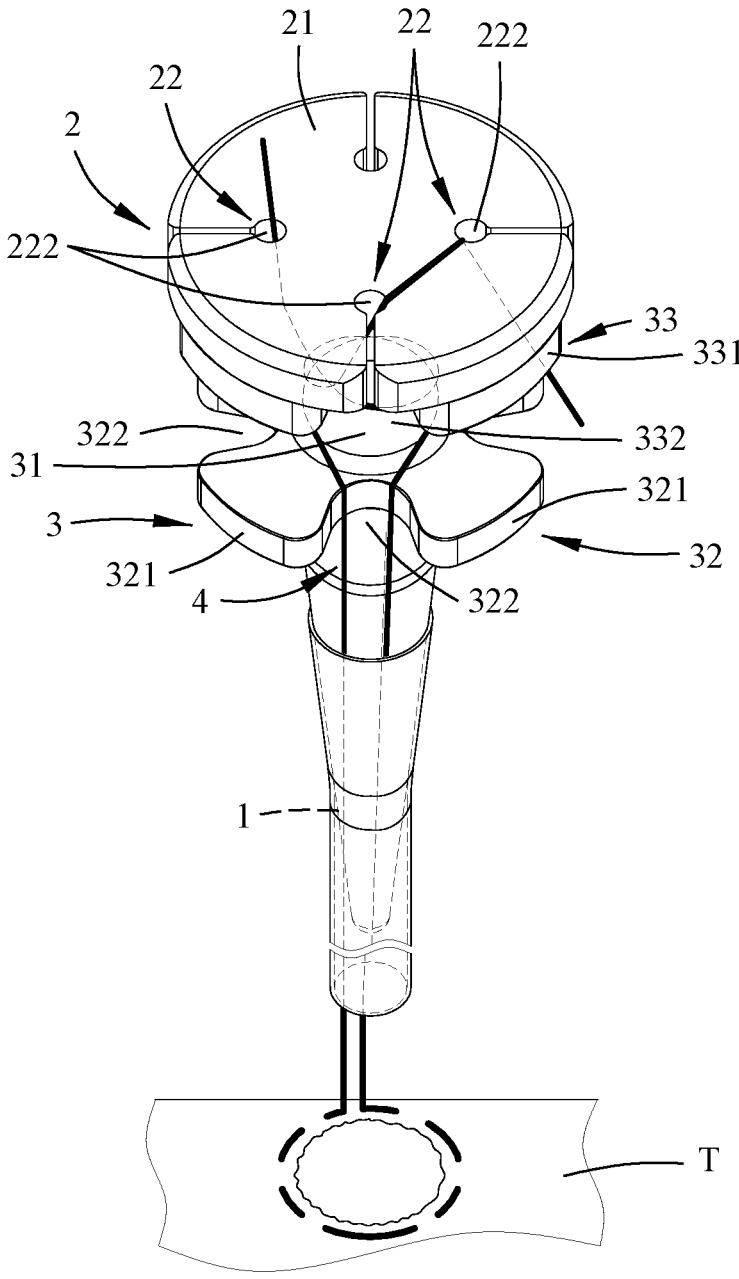
FIG. 5 is a schematic view illustrating the embodiment holding the surgical suture in another different manner.

Referring further to FIG. 5, it is noted that, to further assure holding effectiveness, the user may wind one of the end sections of the surgical suture around at least any two of the holding slots 22 (i.e., the one of the end sections of the surgical suture may be wound around all four of the holding slots 22). In addition, the user may wind each of the end sections of the surgical suture around at least any two of the holding slots 22.

Figure 6:
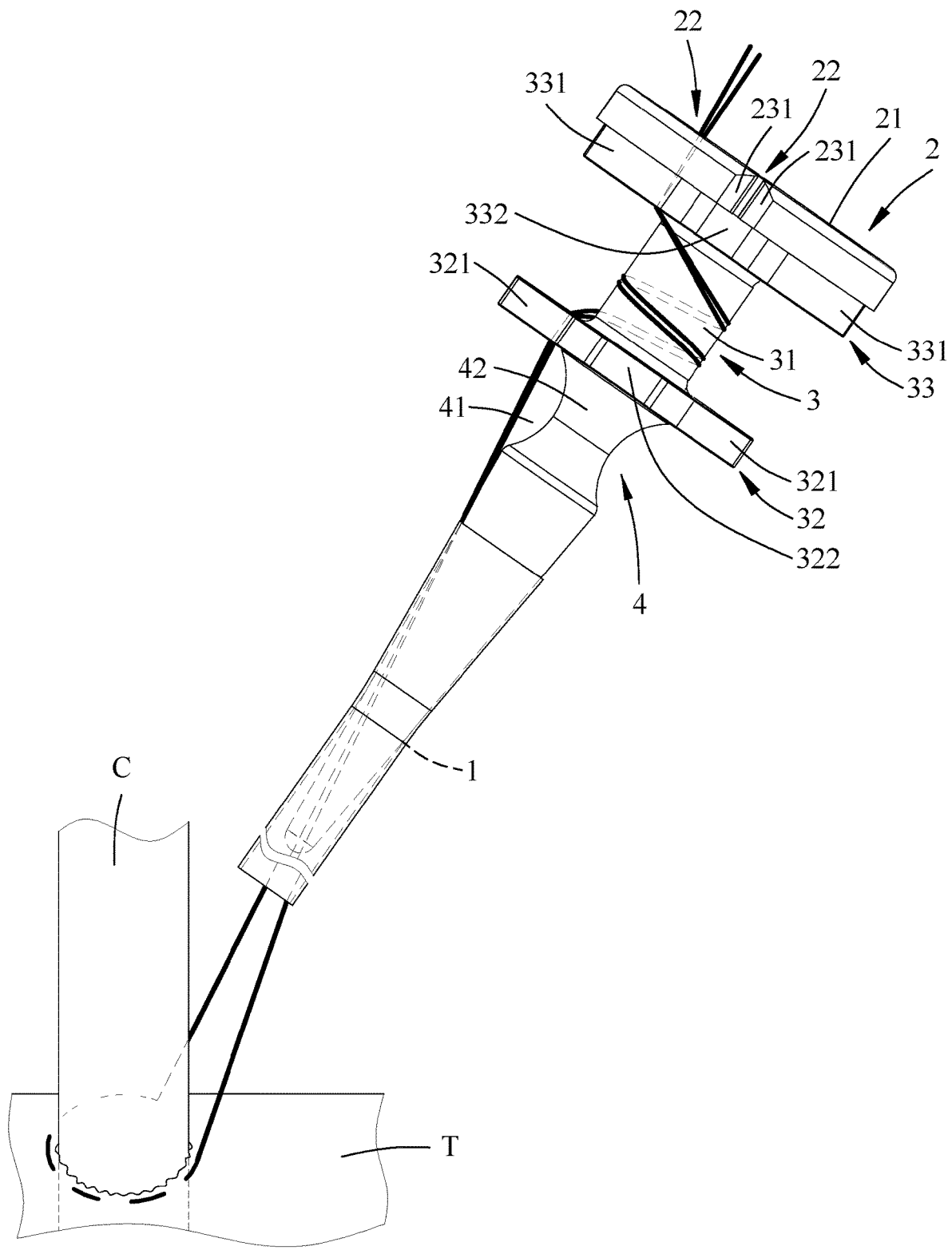
FIG. 6 is a schematic view illustrating the embodiment holding the surgical suture while the surgical suture ties a cannula to a patient's body tissue.

Referring further to FIG. 6, the surgical suture holder may also be used in a surgery involving cannula fixation. In this case, the patient's body tissue (T) is a vessel, and a cannula (C) is inserted into a surgical incision of the vessel. Both of the cannula (C) and the surgical incision of the vessel are surrounded by the interconnecting section of the surgical suture. When the surgical suture is pulled and tightened, the surgical incision of the vessel is narrowed and the surgical suture ties the cannula (C) to the vessel. Afterwards, the surgical suture holder is securely inserted into the opening of the tubular object so that the user may further pull tight the end sections of the surgical suture, wind the end sections of the surgical suture around the winding portion 31 of the winding section 3, and engage the end sections of the surgical suture into the respective one of the holding slots 22. Consequently, the cannula (C) is fixed to the patient's body tissue (T).

When removing the surgical suture, by virtue of the cutting recess 41, and by virtue of the tension of the surgical suture being maintained, the user may easily cut the end sections of the surgical suture at a position between the first blocking board 32 and the insertion section 1. Afterwards, the end sections of the surgical suture may be unwound from the winding portion 31 of the winding section 3 and released from at least one of the holding slots 22 that holds the end sections of the surgical suture. Then, the user may throw away the used end sections of the surgical suture.

In summary, the compactness of the surgical suture holder provides extra surgical room to ease an intended surgical operation, and a surgeon may carry out the surgery requiring a plurality of the surgical suture holders and still has enough room for a safe operation. That is to say, the surgeon does not need to make an incisive opening bigger than necessary on the patient. When the surgery involves a thoracotomy and when the surgeon has to temporarily close a thoracic surgical field, it is relatively easy for the surgeon to close the thoracic surgical field entirely while leaving the suture holder(s) within the thorax, thus reducing the intraoperative risk of infection. Furthermore, by virtue of holding slots 22, the surgical suture is not only clamped between the opening of the tubular snaring object and the insertion section 1 of the surgical suture holder, but is doubly held in place by the surgical suture holder when the surgical suture is wound around the winding section 31 and the holding slots 22. Therefore, the surgeon may carry out the surgery in a smoother and safer manner, hence reducing the risk of the surgery.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A surgical suture holder adapted to be disposed on an opening of a tubular snaring object and adapted for holding at least one surgical suture, the surgical suture holder extending along a holder axis and comprising:

an insertion section adapted to be inserted into the opening of the tubular snaring object and being tapered toward the tubular snaring object; and a holding section having a holding board that has a periphery surrounding the holder axis, and at least one holding slot that is recessed from the periphery of the holding board, that extends through the holding board in an extending direction of the holding axis, and that is adapted for the at least one surgical suture to fit thereinto so that the at least one holding slot holds the at least one surgical suture; and a winding section located between the insertion section and the holding section, the winding section including a winding portion that is adapted to be wound around by the at least one surgical suture, and a first blocking board that is located between the winding portion and the insertion section, the first blocking board having a board body that has a periphery surrounding the holder axis, and at least one groove that is recessed from the periphery of the board body and that extends through the board body in the extending direction of the holder axis, the at least one surgical suture extending through the at least one groove of the first blocking board when being held by the at least one holding slot;

wherein the winding section further includes a second blocking board that is located between the winding portion and the holding section, the second blocking board having a board body that has a periphery surrounding the holder axis, and at least one groove that is recessed from the periphery of the board body of the second blocking board, that extends through the board body of the second blocking board in the extending direction of the holder axis, and that is in spatial communication with the at least one holding slot of the holding section, the at least one surgical suture extending through the at least one groove of the second blocking board when being held by the at least one holding slot;

wherein the holding board is made of a resilient material, and is disposed on the board body of the second blocking board; and wherein the holding board and the second blocking board are made of different materials.

2. The surgical suture holder as claimed in claim 1, wherein the at least one holding slot has a slot neck part that is connected to the periphery of the holding board and that has a width adapted to be smaller than a diameter of the at least one surgical suture before the holding board is deformed, and a slot head part that is in spatial communication with the slot neck part and that is adapted for accommodating the at least one surgical suture.

3. The surgical suture holder as claimed in claim 1, wherein the at least one holding slot includes a plurality of holding slots, the at least one groove of the first blocking board including a plurality of grooves that respectively correspond in position to the plurality of holding slots in the extending direction of the holder axis, the at least one groove of the second blocking board including a plurality of grooves that respectively correspond in position to the plurality of holding slots in the extending direction of the holder axis.

4. The surgical suture holder as claimed in claim 1, further comprising a cutting section that is located between the insertion section and the winding section, the cutting section having a concave surface that defines a cutting recess, the at least one surgical suture hanging over the concave surface when the at least one surgical suture extends across the cutting recess.

5. The surgical suture holder as claimed in claim 4, wherein the concave surface of the cutting section surrounds the holder axis such that an area of a cross section of the cutting section decreases and then increases as the cutting section extends from the insertion section to the winding section.

6. The surgical suture holder as claimed in claim 1, wherein the holding section further has at least one slot-defining surface that defines the at least one holding slot, the at least one slot-defining surface having two guiding parts that are located at the periphery of the holding board, that are spaced apart from each other, and that are adapted for guiding the at least one surgical suture into the at least one holding slot.

7. The surgical suture holder as claimed in claim 1, wherein the holding board is configured to be disc-shaped.

* * * * *